United States Patent
Figueroa et al.

(10) Patent No.: US 11,835,532 B2
(45) Date of Patent: *Dec. 5, 2023

(54) GREEN CONCENTRATED REAGENT FOR HEMOTOLOGY SYSTEMS

(71) Applicant: BECKMAN COULTER, INC., Brea, CA (US)

(72) Inventors: Ignacio Figueroa, Miami, FL (US); Jing Li, Palmetto Bay, FL (US); Nery Ortiz, Miami, FL (US); Wayne Goldson, Punta Gorda, FL (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/963,936

(22) Filed: Oct. 11, 2022

(65) Prior Publication Data

US 2023/0047876 A1 Feb. 16, 2023

Related U.S. Application Data

(63) Continuation of application No. 17/053,407, filed as application No. PCT/US2019/032858 on May 17, 2019, now Pat. No. 11,519,921.

(60) Provisional application No. 62/672,869, filed on May 17, 2018.

(51) Int. Cl.
*G01N 33/50* (2006.01)
*G01N 33/49* (2006.01)
*G01N 33/72* (2006.01)

(52) U.S. Cl.
CPC ....... *G01N 33/721* (2013.01); *G01N 33/5002* (2013.01); *G01N 33/5094* (2013.01); *G01N 33/49* (2013.01); *Y10T 436/10* (2015.01); *Y10T 436/101666* (2015.01); *Y10T 436/107497* (2015.01); *Y10T 436/108331* (2015.01)

(58) Field of Classification Search
CPC ........... G01N 33/5002; G01N 33/5094; G01N 33/49; G01N 33/491; G01N 33/721; G01N 33/80; Y10T 436/10; Y10T 436/101666; Y10T 436/105831; Y10T 436/106664; Y10T 436/107497; Y10T 436/108331; Y10T 436/25625
USPC ............. 436/10, 15, 16, 17, 18, 63, 66, 179; 422/73

See application file for complete search history.

(56) References Cited

U.S. PATENT DOCUMENTS

| | | | | |
|---|---|---|---|---|
| 5,227,304 | A * | 7/1993 | Wong | G01N 33/5094 436/179 |
| 5,882,934 | A * | 3/1999 | Li | G01N 33/721 436/15 |
| 5,935,857 | A * | 8/1999 | Riesgo | G01N 33/5002 436/63 |
| 6,706,526 | B2 * | 3/2004 | Lang | G01N 33/5094 436/66 |
| 11,519,921 | B2 * | 12/2022 | Figueroa | G01N 33/80 |
| 2012/0034640 | A1 * | 2/2012 | Goldson | C12Q 1/06 435/29 |
| 2014/0273061 | A1 * | 9/2014 | Wu | G01N 21/47 435/29 |

FOREIGN PATENT DOCUMENTS

| | | |
|---|---|---|
| JP | 2001-512238 | 8/2001 |
| JP | 4838300 | 8/2008 |
| JP | 2020517286 | 6/2020 |

OTHER PUBLICATIONS

Notification Concerning Transmittal of PCT International Preliminary Report on Patentability for PCT Patent Application No. PCT/US2019/032858, 7 pages, dated Nov. 26, 2020.

Japan Patent Office, Official Action, regarding Application No. 2020-564495, 12 pages, dated Feb. 17, 2023.

* cited by examiner

*Primary Examiner* — Maureen Wallenhorst
(74) *Attorney, Agent, or Firm* — McAndrews, Held & Malloy, Ltd.

(57) ABSTRACT

Environmentally-friendly, aqueous concentrated reagent compositions are provided for dilution and use in suitable hematology analyzers for analyzing blood cells including for enumeration and sizing of blood cells, determination of hemoglobin parameters and differentiation of leukocyte subpopulations in a single blood cell sample.

20 Claims, No Drawings

GREEN CONCENTRATED REAGENT FOR HEMOTOLOGY SYSTEMS

RELATED APPLICATIONS

The present patent application is a continuation of U.S. patent application Ser. No. 17/053,407, filed Oct. 6, 2020, now U.S. Pat. No. 11,519,921, which is a 35 U.S.C. 371 U.S. National Phase application of International Patent Application No. of PCT/US2019/032858 filed May 17, 2019, claiming the benefit of priority to U.S. Provisional application Ser. No. 62/672,869, filed May 17, 2018. The entire text of the aforementioned applications is incorporated herein by reference in its entirety.

BACKGROUND OF THE DISCLOSURE

Field of the Disclosure

Environmentally-friendly, aqueous green concentrated sample reagent compositions are provided for use in suitable hematology analyzers for analyzing blood cells including for enumeration and sizing of blood cells, determination of hemoglobin parameters and differentiation of leukocyte subpopulations in a single blood cell sample.

Description of the Related Art

One problem with some hematology analyzers is the need to frequently replenish the sample diluent container. For example, when the sample diluent is manufactured and sold at working concentration, an ultra-high volume lab might need to make several changes in a high volume hospital in a single day of work. The storage space and the laboratory foot print are limited in many clinical labs making it challenging to keep large quantities of diluent at hand and/or store used containers until they can be removed from the lab. Another problem is that certain prior art blood sample diluents may form up to 150 ppm formaldehyde in the waste stream which may cause environmental concerns.

Attempts to simply prepare more concentrated forms of prior art sample diluents have been hampered by maximum concentration factors. For example, one commercially available blood diluent composition for use with certain hematology analyzers was found to have a maximum of 6×concentration factor because of limited component solubility.

In many cases diluents designed for different hematology analyzers may not be used interchangeably due to different hardware, chemistry volumes, reaction times, and software algorithms.

U.S. Pat. No. 5,935,857 discloses an isotonic blood diluent for use in blood cell analysis, the diluent containing EDTA, imidazole, alkaline metal chloride, alkaline metal sulfate and an antimicrobial.

U.S. Pat. No. 6,706,526 discloses a low formaldehyde aqueous blood diluent containing disodium EDTA, sodium chloride, sodium sulfate, procaine, N-(2-acetoamido)iminodiacetic acid, and various low formaldehyde producing antimicrobials.

U.S. Pat. No. 5,834,315 discloses a lytic reagent comprising a quaternary ammonium salt and/or a pyridinium salt in an amount effective to lyse erythrocytes for determining total hemoglobin in blood.

Stable aqueous concentrated reagents that exhibit low formaldehyde formation, both as manufactured and over time in waste stream effluent, are desirable, particularly for use as sample diluents in hematology analyzer instrumentation.

SUMMARY OF THE INVENTION

Environmentally-friendly, low-formaldehyde aqueous green concentrated aqueous reagent compositions and methods are provided.

An aqueous green concentrated sample reagent composition is provided which may be used, for example, as a body fluid sample diluent for use in a hematology analyzer or cellular analyzer, the concentrated reagent composition comprising a chelating agent, a hemoglobin ligand, a stabilizing agent, a buffer, and an antimicrobial agent.

An aqueous green concentrated sample reagent composition is provided which may be used, for example, as a body fluid sample diluent for use in a hematology analyzer or cellular analyzer, the concentrated reagent composition comprising a chelating agent, a hemoglobin ligand, a stabilizing agent, a buffer, and an antimicrobial agent, wherein the concentrated reagent composition remains clear and colorless in from a 10-fold to a 20-fold concentration factor compared to a working concentration reagent composition, when stored at a temperature from 2-30° C., for at least one year from date of manufacture. The aqueous green concentrated reagent composition comprises or produces less than about 2 parts per million (ppm) of formaldehyde over a period of time of at least 1 year when stored at ambient temperature. The aqueous green concentrated reagents may improve the efficiency of hematology analyzers by reducing storage requirements and shipping costs, and reducing environmental impact.

The aqueous green concentrated reagent compositions may include a chelating agent, for example, an EDTA sodium salt such as tetrasodium EDTA.

The aqueous green concentrated reagent compositions may include a hemoglobin ligand selected from the group consisting of imidazole, phenylimidazole, methylimidazole, ethylimidazole, and butylimidazole. The aqueous green concentrated reagent composition may include imidazole as the hemoglobin ligand.

The aqueous green concentrated reagent compositions may include one or more stabilizing agents selected from alkaline metal sulfates and/or alkaline metal halides, for example, alkaline metal sulfate stabilizing agents such as sodium sulfate and/or potassium sulfate, for example, comprising sodium sulfate and potassium sulfate in a weight ratio of from 0.5:1 to 3:1; or from 1:1 to 3:1.

The aqueous green concentrated reagent compositions may be diluted with water to provide a working concentration reagent composition, which may include from about 25 to about 75 mmol total stabilizing agent, or from about 30 to about 60 mmol total stabilizing agent.

The aqueous green concentrated reagent compositions may comprise a working concentration reagent composition from 25 to 75 mmol total sulfate ion.

The aqueous green concentrated reagent compositions may include a buffer comprising one or more of potassium sodium tartrate, potassium hydrogen phosphate, sodium hydrogen phosphate, or a hydrate thereof.

The aqueous green concentrated reagent compositions may include one or more antimicrobial agents selected from the group consisting of 5-fluorouracil, 5-chloro-2-methyl-4-isothiazolin-3-one (CMIT), 2-methyl-4-isothiazolin-3-one (MIT), 5-bromo-5-nitro-1,3-dioxane (Bronidox L), polyaminopropyl biguanide (Cosmocil CQ®), 1,2-benzisothiazolin one (BIT), 4,5-dichloro-2-n-octyl-4-isothiazolin-3-one (DCOIT), 2-n-octyl-4-isothiazolin one (OIT), ortho-phthaldialdehyde (OPA), and 1,2 dibromo-2,4 dicyanobutane (Bromothalonil).

The aqueous green concentrated reagent compositions may include a combination of antimicrobial agents including 5-chloro-2-methyl-4-isothiazolin-3-one (CMIT), 2-methyl-4-isothiazolin-3-one (MIT), 5-fluorouracil, and 5-bromo-5-nitro-1,3-dioxane.

The aqueous green concentrated reagent compositions may include one or more of an alkaline metal chloride (e.g., NaCl, KCl), a platelet stabilizing agent (e.g, procaine, tetracaine), and an osmotic stabilizing agent (e.g., glycerol).

The aqueous green concentrated reagent compositions may include an alkaline metal chloride selected from the group consisting of NaCl and KCl.

The aqueous green concentrated reagent compositions may include a platelet stabilizing agent selected from the group consisting of procaine and tetracaine.

The aqueous green concentrated reagent compositions may include glycerol as an osmotic stabilizing agent.

The aqueous green concentrated reagent compositions may be diluted with water by a dilution factor of 10-fold to 20-fold to form a working concentration reagent composition, such that the working concentration reagent compositions exhibit each of: i) pH in the range of from pH 6.90 to 7.30 at ambient temperature; ii) conductivity in the range of from 19 to 20 mS/cm at ambient temperature; and iii) osmolality in the range of from 315 to 360 mOsm/Kg at ambient temperature.

An aqueous green concentrated reagent composition is provided comprising 10 to 100 g/L tetrasodium EDTA; 20 to 50 g/L imidazole; 30 to 90 g/L sodium sulfate; 20 to 60 g/L potassium sulfate; 60 to 300 g/L sodium potassium tartrate; and an antimicrobial agent selected from the group consisting of 5-chloro-2-methyl-4-isothiazolin-3-one (CMIT), 2-methyl-4-isothiazolin-3-one (MIT), 5-bromo-5-nitro-1,3-dioxane (Bronidox L), and 5-fluorouracil.

An aqueous green concentrated reagent composition is provided comprising 10 to 100 g/L tetrasodium EDTA; 10 to 50 g/L imidazole; 20 to 100 g/L sodium sulfate; 15 to 60 g/L potassium sulfate; 60 to 300 g/L sodium potassium tartrate; and an antimicrobial agent selected from the group consisting of 5-chloro-2-methyl-4-isothiazolin-3-one (CMIT), 2-methyl isothiazolin-3-one (MIT), 5-bromo-5-nitro-1,3-dioxane (Bronidox L), and 5-fluorouracil.

An aqueous green concentrated reagent composition is provided comprising 40 to 60 g/L tetrasodium EDTA; 20 to 45 g/L imidazole; 60 to 85 g/L sodium sulfate; 20 to 40 g/L potassium sulfate; 80 to 150 g/L sodium potassium tartrate, optionally further comprising one or more of 40 to 60 g/L sodium phosphate monobasic, 20 to 60 g/L sodium chloride, and 5 to 15 g/L 5-fluorouracil.

An aqueous green concentrated reagent composition is provided comprising 10 to 65 g/L tetrasodium EDTA; 15 to 50 g/L imidazole; 40 to 100 g/L sodium sulfate; 15 to 50 g/L potassium sulfate; and 80 to 180 g/L sodium potassium tartrate.

The aqueous green concentrated reagent compositions may include one or more antimicrobial agents selected from the group consisting of 5-chloro-2-methyl-4-isothiazolin-3-one (CMIT), 2-methyl-4-isothiazolin-3-one (MIT), 5-bromo-5-nitro-1,3-dioxane (Bronidox L), and 5-fluorouracil.

A method is provided for analyzing a body fluid comprising: a) diluting an aqueous green concentrated reagent composition according to the disclosure from 10-fold to 20-fold to form a working concentration reagent composition; b) mixing a body fluid with the working reagent composition to form a diluted body fluid sample.

A method is provided for analyzing a blood sample containing blood cells comprising: a) diluting an aqueous green concentrated reagent composition according to the disclosure from 10-fold to 20-fold to form a working concentration reagent composition; b) mixing a blood sample containing blood cells with the working reagent composition to form a diluted blood sample, wherein the chelating agent and the hemoglobin ligand are in an amount effective to provide reproducible hemoglobin and cell volume measurements over a temperature range from 15° C. to 32° C.; and c) analyzing said diluted blood sample to determine a physical parameter of said blood cells.

A method is provided for analyzing a blood sample containing blood cells comprising: a) diluting an aqueous green concentrated reagent composition according to the disclosure from 10-fold to 20-fold to form a working concentration reagent composition; b) mixing a blood sample containing blood cells with the working reagent composition to form a diluted blood sample, c) mixing a lytic reagent with said diluted blood sample to lyse red blood cells prior to analyzing said diluted blood sample, wherein the chelating agent and the hemoglobin ligand are in an amount effective to provide reproducible hemoglobin and cell volume measurements over a temperature range from 15° C. to 32° C.; and d) analyzing said diluted blood sample with added lytic reagent to determine a physical parameter of said blood cells.

A method is provided for analyzing a blood sample containing blood cells comprising: a) diluting an aqueous green concentrated reagent composition according to the disclosure from 10-fold to 20-fold to form a working concentration reagent composition; b) mixing a blood sample containing blood cells with the working reagent composition to form a diluted blood sample, c) adding a lyse reagent to lyse the RBC releasing hemoglobin, wherein the chelating agent and the hemoglobin ligand are in an amount effective to provide reproducible hemoglobin and cell volume measurements over a temperature range from 23° C. to 32° C.; and d) analyzing said diluted blood sample with added lyse reagent to determine a physical parameter of said blood WBC cells and hemoglobin concentration on an automatic hematology analyzer.

In the methods, the blood cells may comprise red blood cells.

In the methods, analyzing a diluted blood sample to determine at least one physical parameter may comprise analyzing to determine mean cell volume of said red blood cells.

In the methods, the blood cells may comprise white blood cells.

In the methods, analyzing a diluted blood sample to determine at least one physical parameter of blood cells may comprise an automated differential analysis of white blood cells to determine at least three subpopulations of white blood cells.

In the methods, analyzing a diluted blood sample to determine at least one physical parameter of blood cells may comprise an automated differential analysis of white blood cells to determine at least five subpopulations of white blood cells.

In the methods, the lytic reagent may comprise an aqueous solution of at least one quaternary ammonium salt.

In the methods, the analyzing a diluted blood sample to determine at least one physical parameter of blood cells may comprise analyzing to determine the number of platelets.

In the methods, the analyzing a diluted blood sample to determine at least one physical parameter of blood cells may comprise analyzing to determine hemoglobin content.

DETAILED DESCRIPTION OF THE INVENTION

A stable aqueous green concentrated reagent composition is provided for preparing a working concentration reagent composition for use in analysis of a body fluid sample, such as a blood sample. The green concentrated reagent composition may be manufactured in at least a 10-fold to 20-fold concentration factor for dilution to provide a working concentration reagent for use as, for example, a blood diluent for the determination of red blood cell, white blood cell, hemoglobin and platelet measurements in a hematology analyzer. The concentrated reagent composition is also environmentally friendly or "green" which means it is cyanide-free and exhibits low formaldehyde levels. The concentrated sample reagents provided herein substantially reduce the need to frequently replace the sample diluent container, and reduce transportation and storage space by at least 10-fold to 20-fold and associated costs compared to prior art sample reagents accordingly.

The green working concentration reagent is useful for dilution and analysis of a body fluid sample, for example, a blood sample. Measurements used in analysis of the blood sample include cell size, shape, content and volume. Measurements can be made using light scatter, low frequency current, radio frequency current, fluorescence and combinations thereof. The reagent may be used for the determination of WBC and differentiation of leukocytes into three subpopulations using impedance measurement.

The design of an environmentally friendly green concentrated reagent, or "GCR" reagent presented several challenges. Because the reagent is intended for use, for example, in an automatic hematology analyzer platform for counting, sizing, diluting, sheath, and takes part in biochemical reactions, as well as for washing, any change to the components could have had an impact basically to any of the measurements performed by the instrument.

Replacement of the antimicrobial cocktail used in predicate diluents was investigated to reduce the formaldehyde content and additional replacement of key ingredients was designed to increase the maximum concentration of the concentrated reagent composition.

Various salts were tested for aqueous solubility and the ability to stay in solution even at temperatures lower than ambient temperature.

In some aspects, the aqueous concentrated reagent composition is useful in a method comprising diluting the concentrated reagent composition with water to provide a working concentration reagent for dilution of a blood sample for the determination of red blood cell, and platelet measurements. Measurements include cell size, shape, content and volume. Measurements can be made using light scatter, low frequency current, radio frequency current, fluorescence and combinations thereof. In another aspect, the concentrated reagent composition and working concentration reagent composition is useful for the determination of WBC and differentiation of leukocytes into three subpopulations and hemoglobin concentration. In a further aspect, the concentrated reagent composition and working concentration reagent composition is useful as a sheath fluid in focused flow cytometry for determination of five subpopulations of leukocytes, NRBC and Retic. In another aspect, the concentrated reagent composition and working concentration reagent composition is useful for fluorescence flow cytometry analysis when using fluorescence probes or antibodies.

The concentrated reagent is shelf stable and can be used over a wide range of operating temperatures. In addition, the working concentration reagent composition can be used with fresh or aged blood samples. Measurements obtained from using the working concentration reagent composition provided herein are comparable to measurements obtained from using a commercially available diluent.

Definitions and Acronyms

The singular forms "a", "an" and "the" are intended to include the plural forms as well, unless the context clearly indicates otherwise.

The term "and/or" refers to and encompasses any and all possible combinations of one or more of the associated listed items.

The term "about," when referring to a measurable value such as an amount of a compound, dose, time, temperature, and the like, is meant to encompass variations of 10%, 5%, 1%, 0.5%, or even 0.1% of the specified amount, and at least industry-standard variation in the test method for measuring the value.

The terms, "patient", "subject" or "subjects" include but are not limited to humans, the term may also encompass other mammals, or domestic or exotic animals, for example, dogs, cats, ferrets, rabbits, pigs, horses, cattle, birds, or reptiles.

The acronym "GCR" refers to Green Concentrated Reagent.

The phrase "green reagent" refers to a cyanide-free and low formaldehyde releasing reagent. The phrases "green concentrated reagent", "aqueous green concentrated reagent" or "aqueous concentrated reagent" are each used herein to refer to an aqueous green concentrated reagent composition that is concentrated in at least 10×, or from 10× to 20×, compared to working concentration.

The term "sample diluent" refers to a composition appropriate for use as a diluent for use with a patient sample. The patient sample may be a body fluid sample obtained from the patient, for example, selected from a blood, urine, saliva, sputum, feces, semen, cerebrospinal fluid, or other sample of body fluids, tissue, or other biological sample. The patient sample may be a biological sample from a swab run over an affected area, such as a throat, nasal, vaginal, cervical, and superficial wound culture, or may be obtained from a needle aspirate of a tissue or wound. In some aspects, the patient sample is a blood sample selected from whole blood, serum, or plasma. In some aspects, the sample is a body fluid control sample, for example, stabilized human blood. In some aspects, the sample reagent is a blood diluent.

The phrases "ready to use reagent", "ready to use reagent composition", "working concentration reagent", and "working concentration reagent composition" refer to an aqueous reagent composition produced at about 1×working concentration appropriate for use, for example, as a sample diluent with a hematology analyzer or cellular analyzer.

The phrase "concentrated reagent", or "concentrated reagent composition", refers to an aqueous green concentrated reagent composition produced at, for example, about a 10-fold to 20-fold concentration factor for dilution with water, such as deionized water, to provide a working concentration reagent composition useful as a blood sample diluent in a hematology analyzer. The concentrated reagent composition may be manufactured and remain stable in a concentration from 10-fold to 20-fold, or at least 10-fold, 11-fold, 12-fold, 13-fold, 14-fold, 15-fold, 16-fold, 17-fold, 18-fold, 19-fold, or 20-fold more concentrated than the working concentration reagent composition. The concentrated reagent composition is stable for at least 3 months, 6 months, 9 months, 12 months, 18 months, 24 months, 30 months or 36 months from the date of manufacture when stored at a temperature within a range of from 2 to 40° C., 2 to 30° C., 15 to 37° C., or at ambient temperature 19 to 27° C.

Stability of aqueous concentrated reagent compositions may be assessed by aqueous dilution to a working concentration reagent composition that is effective for use as blood diluent in a hematology analyzer, wherein working concentration reagent composition exhibits i) pH in the range of from pH 6.90 to 7.30 at ambient temperature; ii) conductivity in the range of from 19 to 20 mS/cm at 25° C.; and iii) osmolality in the range of from 315 to 360 mOsm/Kg at ambient temperature. Stability may be further assessed by lack of visual precipitation, clarity, colorlessness, and/or lack or microbial growth. Clarity may be assessed by, for example, Completeness of Solution Test under USP<641>. Colorlessness may be assessed by, for example, Color of Solution or degree of Coloration test under Ph Eur 2.2.2. Lack of visual precipitation may be assessed by, for example, Visible Particle test under USP<790>. Lack of microbial growth may be assessed by, for example, not more than 10 cfu/100 mL Total Yeast and Molds Count (TYMC) by USP<61>.

An "nX concentrated reagent", or "nX concentrated reagent composition" refers to a concentrated composition which when diluted by a dilution factor of X provides a working concentration reagent composition, where X is a number selected from 10 to 20, or any number in between. For example, where n=15, a 15× concentrated reagent refers to concentrated reagent composition produced at 15 times more concentrated (15×) than working concentration reagent composition. For example, a 15× concentrated reagent composition may be diluted to provide 1×working concentration reagent appropriate for use as a sample diluent, for example, a blood diluent for use in a hematology analyzer, or a body fluid sample diluent in a cellular analyzer.

The phrase "1×— reagent" refers to working concentration reagent composition, for example, at a concentration suitable for use in diluting a body fluid sample, for example, a blood sample for use in a hematology analyzer, or a body fluid sample for use in a cellular analyzer. Dilution of the concentrated reagent to provide a 1×reagent at working concentration may be performed in an automated fashion by a diluter unit or by manual dilution.

The phrase "10×— concentrated reagent" refers to a concentrated composition that is diluted 10-fold to provide a working concentration reagent appropriate for use, for example, as a blood diluent.

The phrase "15×— concentrated reagent" refers to a concentrated composition that is diluted 15-fold to provide a working concentration reagent appropriate for use, for example, as a blood diluent.

The phrase "18×— concentrated reagent" refers to a concentrated composition that is diluted 18-fold to provide a working concentration reagent appropriate for use, for example, as a blood diluent.

The phrase "20×— concentrated reagent" refers to a concentrated composition that is diluted 20-fold to provide a working concentration reagent appropriate for use, for example, as a blood diluent.

The term "DxH System" refers to COULTER® DxH 800/600 System which is a quantitative, multi-parameter, automated hematology analyzer for in vitro diagnostic used in screening patient populations found in clinical laboratories. Samples to be analyzed include whole blood samples, for example, whole blood specimens collected in EDTA anticoagulant. The DxH system is used to quantitatively evaluate hematology parameters including CBC, WBC differentials, Retic and body fluids, e.g. WBC (white blood cell count), RBC (red blood cell count), HGB (hemoglobin), MCV (mean corpuscular volume), RDW (red blood cell distribution width), RDW-SD (red blood cell distribution), PLT (platelets), MPV (mean platelet volume), NE (neutrophils), LY (lymphocytes), MO (monocytes), EO (eosinophils), BA (basophils), NRBC (nucleated red blood cells), RET (reticulocytes), MRV (mean reticulocyte volume), IRF (immature reticulocyte fraction), or combinations thereof.

The term "diluter unit" refers to a reagent preparation instrument. The diluter unit dilutes the concentrated reagent to a 1×working concentration reagent, for example, by using conductivity as the measuring parameter. In this context it may be desirable to establish the limits of conductivity, or another parameter, for providing the working concentration reagent composition.

The term "lytic reagent", refers to hemolytic reagent used to lyse erythrocytes and prepare a sample containing predominantly or solely leukocytes. The lytic reagent may be tailored for use with a particular working concentration reagent.

The abbreviation "fL" refers to femtoliter ($10^{-15}$ L).

The term "mean corpuscular volume" (MCV) is the average volume of red cells in a specimen. MCV is elevated or decreased in accordance with average red cell size; i.e., low MCV indicates microcytic (small average RBC size), normal MCV indicates normocytic (normal average RBC size), and high MCV indicates macrocytic (large average RBC size). The reference range for MCV is 80-96 fL/red cell in adult. Reference ranges may vary depending on the individual laboratory and patient's age.

The term "red cell distribution width" (RDW) is a parameter that measures variation in red blood cell size or red blood cell volume. RDW is elevated in accordance with variation in red cell size (anisocytosis), i.e, when elevated RDW is reported on complete blood count, marked anisocytosis (increased variation in red cell size) is expected on peripheral blood smear review.

The acronym "RBC" refers to red blood cells.

The acronym "CBC" refers to complete blood count.

The acronym "RDW-SD" refers to red cell distribution width standard deviation.

The acronym "RDW-CV" refers to red cell distribution width coefficient of variation.

The acronym "IVD" refers to in vitro diagnostic.

Reagent Parameters for Investigation

Reagent parameters studied in development of the new concentrated reagent compositions include conductivity, pH, osmolality, particle count, and some CBC parameters in hematology analyzers, for example, MCV, RDW and RDW, WBC three part histogram and the modality of the Lymphocyte and Granulocyte population.

A diluter unit may be employed to dilute the concentrated reagent to 1×working concentration reagent, for example, by using conductivity as the measuring parameter, so it may be desirable to establish the limits of this parameter for the new reagent at working concentration. In the predicate diluent, the conductivity was not adjusted, and was a consequence of the osmolality final adjustment value.

The phrase "ambient temperature" refers to 19-27° C.

The phrase "low formaldehyde" refers to formaldehyde concentrations in reagent compositions or waste solutions produced therefrom having or producing less than about 2 parts per million (ppm) of formaldehyde over a period of time of at least 1 year from the date of manufacture. In one aspect, low formaldehyde concentrated reagents are provided having or producing not more than about 2.0 ppm, 1.5 ppm, 1.0 ppm, or 0.5 ppm of formaldehyde over a period of time of at least 1 year. Formaldehyde can be measured using EPA method 8315A. This method entails derivitizing the sample with 2,4-dinitrophenylhydrazine to convert the carbonyl groups of aldehydes present to the hydrazones. Each carbonyl compound present in the sample forms a separate hydrazone derivative and these individual derivatives are extracted from the solution using an organic solvent. The individual hydrazone derivatives are separated and quantified by HPLC (High Performance Liquid Chromatography). The details of EPA method 8315A can be obtained from the EPA website.

The phrase "formaldehyde-free" refers to formaldehyde concentrations in reagent compositions or waste solutions produced therefrom having or producing less than about 1 part per million (ppm), 0.5 ppm, 0.1 ppm or less of formaldehyde over a period of time of at least 1 year from the date of manufacture.

The phrase "cyanide-free" refers to cyanide concentrations in reagent compositions or waste solutions produced therefrom having or producing less than about 0.2 parts per million (ppm) of total cyanide over a period of time of at least 1 year. Total cyanide can be measured using EPA method 335.4.

All patents, patent applications and publications referred to herein are incorporated by reference in their entirety.

Some commercially available prior art reagents for use in automated cellular analyzers or hematology analyzers produce formaldehyde in amounts in excess of about 400 parts per million. Formaldehyde has been classified as a known human carcinogen by the WHO International Agency for Research on Cancer (IARC), and is also considered toxic and allergenic at some concentrations. Increasingly, regulatory agencies in states like California and Massachusetts have been restricting the amount of formaldehyde allowed in industrial and medical waste. According to these regulations, formaldehyde concentrations in waste equal to or less than 1 part-per-million is considered formaldehyde-free. Consequently, reagents for use in automated and semi-automated cellular and hematology analyzers that produce less than 1 part-per-million (ppm) of formaldehyde over the course of their shelf-life, or for at least one year post-manufacture, are highly desirable.

Chelating Agents

Aqueous green concentrated and green working concentration reagents are provided comprising one or more chelating agents. A chelating agent is a compound that chelates ions in cell membranes and weakens them, making the cell more susceptible to biocides. Thus, the chelating agent assists the antimicrobial compounds in the composition in killing bacteria and fungi. The chelating agent can also work in conjunction with the buffer to maintain the pH of the composition. In the case where the cellular sample is a blood sample, the chelating agent may also help to maintain anticoagulation of the blood by reducing platelet aggregation.

The chelating agent may include triacetate, tetraacetate or pentaacetate substituents. Thus, for example, the chelating agent may be an ethylenediamine tetraacetic acid (EDTA), an EDTA derivative, such as an EDTA salt, or combinations thereof. The EDTA derivatives may include salts of EDTA, such as sodium and/or potassium salts of EDTA. The chelating agent may be selected from disodium EDTA, tetrasodium EDTA, dipotassium EDTA, tetrapotassium EDTA, ethyleneglycol-bis-(3-aminoethylether)N—N-tetraacetic acid, and ethyleneglycol-bis-(2-aminoethyl ether)N,N,N',N'-tetraacetic acid (EGTA) or a disodium salt thereof (disodium EGTA). Disodium EDTA, when dissolved in water exhibits a pH of less than pH 7. Tetrasodium EDTA when dissolved in water exhibits a pH of greater than pH 7. Therefore, the selection of chelating agent may influence the selection of additional agents when providing a reagent due to pH effects. The pH of 5% disodium EDTA dissolved in water at 25° C. may be within about pH 4 to 6. Disodium EDTA may be used in an anhydrous or a hydrate form, for example, disodium EDTA dihydrate. The pH of a 1% tetrasodium EDTA in water at 25° C. may be within about pH 10.7 to 11.7. The tetrasodium EDTA may be utilized as an anhydrous or hydrate form, such as tetrasodium EDTA dihydrate.

In some aspects, additional chelating agents other than EDTA or its derivatives may be added to the composition of the present invention. Such additional chelating agents include compounds that chelate ions as described above, which are known to those skilled in the art. Some of these chelating agents include, without limitation, cyclohexanediamine-tetraacetic acid, diethylentriaminepentaacetic acid, and/or hydroxyethylethylene-diaminetriacetic acid.

The concentration of each chelating agent in the working reagent composition may be from about 0.5 to about 5.0 grams per liter (g/L), about 2 to about 4 g/L, or about 2.7 to about 3.3 g/L.

The concentration of each chelating agent in the concentrated reagent composition may be from about 5 to about 100 grams per liter (g/L), about 20 to about 60 g/L, or from about 27 to about 50 g/L.

Hemoglobin Ligands

Aqueous green concentrated reagent compositions and green working concentration reagents are provided comprising one or more hemoglobin ligands. The hemoglobin ligand may be selected from 1,2,4-triazole, Allantoin ((2,5-dioxo-4-imidazolidinyl)urea), malic acid, malonic acid, ethylene diamine, N,N-diethylethylene diamine, N,N'-diethylethylene diamine, diethylene triamine, tetraethylene pentamine, 1,6-hexanediamine, 1,3-pentanediamine, 2-methylpentamethylenediamine, 1,2-diaminocyclohexane, 4-aminoacetophenone, bis-hexamethylenetriamine, pyridazine, 3,6-dihydroxypyridazine, Tiron (sodium catechol sulfate; 1,2-dihydroxybenzene-3,5-disulfonic acid disodium salt), 8-hydroxyquinoline, bipyridine, 1,10-phenanthroline, salicylic acid, bisphenol A, pyrazole, 1-phenyl-3-pyrazoline, 3-methyl-1-phenyl-5-pyrazoline, imidazole, and imidazole derivatives. The hemoglobin ligand may be selected from imidazole or an imidazole derivative, for example, selected from phenylimidazole, methylimidazole, ethylimidazole and butylimidazole. Working concentration reagents may include one or more hemoglobin ligands which may be in a concentration of from about 1 to about 4 g/L, about 2 to about 3.5 g/L, or about 2.5 to about 3 g/L, or about 2.7 to 2.9 g/L. Concentrated reagent compositions may include one or more hemoglobin ligands which may be in a concentration of from about 10 to about 80 g/L, about 20 to about 60 g/L or about 40 to about 45 g/L.

Stabilizing Agents

Aqueous green concentrated reagent compositions and green working concentration reagents are provided comprising one or more, or two or more stabilizing agents. The stabilizing agents may be selected from alkaline metal sulfates and/or alkaline metal halides.

The stabilizing agents may be selected from one or more alkaline metal halide stabilizing agents and/or one or more alkaline metal sulfate stabilizing agents. The alkaline metal sulfate stabilizing agent may be selected from one or more, two or more, or three or more of sodium sulfate, sodium hydrogen sulfate (sodium bisulfate), potassium sulfate, and potassium hydrogen sulfate (potassium bisulfate). Concentrated reagent compositions may include potassium sulfate. Concentrated reagent compositions may include both sodium sulfate and potassium sulfate. Concentrated reagent compositions may include sodium sulfate, potassium sulfate, and/or potassium bisulfate. A combination of sodium sulfate and potassium sulfate may be employed in a weight ratio of from 0.5:1 to 3:1; or from 1:1 to 3:1. Working concentration reagent compositions may include from about 20 to about 80 mmol, about 30 to about 70 mmol, or from about 40 to about 60 mmol total alkaline metal sulfate stabilizing agent. In a further aspect, concentrated reagents are provided comprising from about 300 to about 900 mmol, about 400 to about 850 mmol, about 600 to about 800 mmol, or from about 700 to about 800 mmol alkaline metal sulfate stabilizing agent.

Aqueous green concentrated reagent compositions and green working concentration reagent compositions are provided optionally comprising alkaline metal halide stabilizing agents. The alkaline metal halide stabilizing agent may be selected from one or more of sodium chloride, potassium chloride, sodium bromide, potassium bromide or combination thereof. The alkaline metal halides may be alkaline metal chlorides, which may be selected from sodium chloride and potassium chloride. In one aspect, working concentration reagents are provided which may include from 0 to about 3.5 g/L, about 1 to about 3 g/L, or about 1.5 to about 2.9 g/L alkaline metal halide(s). In another aspect, working concentration reagents are provided which may include from 0 to about 70 g/L, about 20 to about 60 g/L, or about 30 to about 55 g/L alkaline metal halide(s).

Buffers

Aqueous green concentrated reagent compositions and green working concentration reagent compositions are provided optionally comprising a buffer agent. The buffer may be used in conjunction with the chelating agent, or other components such as the hemoglobin ligand, and/or sulfate stabilizing agent in appropriate concentrations to maintain the pH of the compositions. The buffer agent may be an alkaline metal salt, or partial alkaline metal salt, of an organic acid or an inorganic acid such as phosphate.

The buffer may include a partial alkaline metal salt, of an organic acid buffer, for example, selected from one or more of sodium, potassium, sodium hydrogen, and/or potassium hydrogen salts of the group consisting of tartrate, citrate, formate, lactate, acetate, and pyruvate and combinations thereof.

The buffer may include a phosphate buffer agent which may be selected from sodium and/or potassium monobasic or dibasic phosphates, or combinations thereof.

The buffer may include sodium and/or potassium, monobasic and/or dibasic salts of tartrate, citrate and/or phosphate, or combinations thereof. For example, the buffer may include one or more of sodium potassium tartrate, sodium phosphate monobasic, sodium potassium tartrate and sodium phosphate monobasic buffer agents. The buffer agents may be employed in an appropriate amount to maintain the pH of the working concentration reagent from pH 6 to 8, 6.5 to 7.5, or 6.9 to 7.3. In general, the buffer agents may be present in a working concentration reagent at from 0 to about 35 g/L, about 5 to about 30 g/L, or about 5 to about 10 g/L. The buffer agents may be present in concentrated reagent at from 0 to about 500 g/L, about 50 to about 300 g/L, or about 90 to about 140 g/L.

An aqueous green working concentration reagent may include sodium potassium tartrate in from 0 to about 30 g/L, about 2 to about 20 g/L, or about 5 to about 8 g/L. A concentrated reagent may include sodium potassium tartrate in from 0 to about 300 g/L, about 20 to about 200 g/L, or about 80 to about 150 g/L.

An aqueous green working concentration reagent may be provided comprising sodium phosphate monobasic in from 0 to about 5 g/L, about 1 to about 4.5 g/L, or about 2.5 to about 4 g/L. A concentrated reagent may include sodium phosphate monobasic in from 0 to about 100 g/L, about 10 to about 80 g/L, or about 45 to about 65 g/L.

An aqueous green concentrated reagent composition may be provided by a process comprising mixing an EDTA Sodium salt, sodium sulfate, potassium sulfate, potassium bisulfate, sodium potassium tartrate, sodium chloride, imidazole and an antimicrobial agent in water. The EDTA sodium salt may be tetrasodium EDTA. The aqueous concentrated reagent process may optionally further comprise adding a buffer, platelet stabilizing agent, osmotic stabilizer, and/or a pH adjusting agent.

The aqueous green concentrated reagent may be manufactured at a particular "concentration factor" selected from at least about a 10-fold to about 20-fold, from 12-fold to 18-fold, or a 10-fold, 11-fold, 12-fold, 13-fold, 14-fold, 15-fold, 16-fold, 17-fold, 18-fold, 19-fold, or 20-fold or more concentrated composition compared to the working concentration reagent, so long as the aqueous concentrated reagent remains stable and suitable for dilution and effective use as a blood sample diluent in a hematology analyzer for a period of at least one year after date of manufacture when stored in a sealed container at a temperature selected from 2 to 30° C.

The term "dilution factor" can be used alone or as the denominator of the fraction, for example a dilution factor of 10 means a 1:10 dilution, or 1 part concentrate in a total of 10 parts of solution. Thus the aqueous concentrated reagent compositions may be diluted with water by an appropriate dilution factor of at least 10, or from 10 to 20 to obtain a working concentration reagent.

The stabilizing agent(s) selected from alkaline metal chloride and alkaline metal sulfate are used to provide a suitable osmolality in the working concentration reagent so as not to adversely affect cell volume. Generally, the working concentration reagent will be isoosmotic. More specifically, the osmolality may be about 200 to 400 milliosmoles (mOsm)/Kg, and preferably from 250 to 380 mOsm/Kg, and most preferably from 315 to 360 mOsm/Kg. However, the osmolality of the working concentration reagent can vary when used with a lytic reagent composition. The volume of the working concentration reagent used to dilute a blood sample can be adjusted relative to a lytic reagent volume so that the final osmolality of the blood sample mixture is between approximately 290 to 350 mOsm, preferably from 310 to 330 mOsm. In addition, when used in a flow instrument, the relationship between the osmolality and conductivity of the sheath fluid and the osmolality and conductivity of the core fluid should be maintained. For example, the working concentration reagent may have conductivity from about 15 to 23 mS/cm, preferably from about 19 to 20 mS/cm.

Antimicrobial Agents

Aqueous green concentrated reagents and green working concentration reagents are provided comprising one or more antimicrobial agents. Compositions provided herein may be stored for extended periods of time before use, and can often be exposed to microorganisms during use. Thus, the compositions provided herein may include one or more antimicrobial agents to eliminate growth of microorganisms prior to and during analysis. However, certain antimicrobial agents used in the compositions known in the art contribute to the production of formaldehyde levels greater than 2 ppm. For use in the composition of this invention, antimicrobial agents should produce low or insubstantial amounts (e.g., preferably, less than 2 ppm, or less than 1 ppm) of formaldehyde for at least one year. The reagents should also provide adequate antimicrobial protection and yet not interfere with the measurement of the cellular sample in the various analytical procedures. Preferably, the antimicrobial agents do not react with other reagents conventionally used in many methods of hematology analyzers.

Green compositions are provided having one or more antimicrobial agents which are effective in preventing growth or eliminating gram negative bacteria, gram positive bacteria, yeast, and/or fungi, and yet which produce in the composition less than 2 ppm, or less than 1 ppm formaldehyde over the course of a year. Preferably, the antimicrobial agents useful in the composition of the invention include a low-formaldehyde releasing or non-formaldehyde releasing antimicrobial agent. In some aspects, the antimicrobial agent is selected from one or more of 5-chloro-2-methyl-4-isothiazolin-3-one (CMIT), 2-methyl-4-isothiazolin-3-one (MIT), 5-bromo-5-nitro-1,3-dioxane (Bronidox L), polyaminopropyl biguanide (Cosmocil CQ®)), 1,2-benzisothiazolin-3-one (BIT), 4,5-dichloro-2-n-octyl-4-isothiazolin-3-one (DCOIT), 2-n-octyl-4-isothiazolin-3-one (OIT), ortho-phthaldialdehyde (OPA), 1,2 dibromo-2,4 dicyanobutane (Bromothalonil), and 5-fluorouracil.

In specific aspects, aqueous green concentrated reagents and green working concentration reagents are provided comprising 5-chloro-2-methyl-4-isothiazolin-3-one (CMIT) and 2-methyl-4-isothiazolin-3-one (MIT) (PROCLIN™ 150). PROCLIN™ 150 is a liquid comprising about 1.46-1.54 wt % total CMIT/MIT wherein CMIT is about 74.5-75.5 wt %, with a specific gravity of 1.2. In one specific aspect, aqueous concentrated reagents and working concentration reagents are provided comprising antimicrobial agents 5-chloro methyl-4-isothiazolin-3-one (CMIT), 2-methyl-4-isothiazolin-3-one (MIT), and 5-fluorouracil. In another specific aspect, aqueous concentrated reagents and working concentration reagents are provided comprising 5-chloro-2-methyl-4-isothiazolin-3-one (CMIT), 2-methyl-4-isothiazolin-3-one (MIT), 5-fluorouracil, and 5-bromo-5-nitro-1,3-dioxane. These antimicrobial agents are commercially available.

Aqueous green concentrated reagent compositions and green working concentration reagent compositions are provided that do not contain N-(Hydroxymethyl)-N-(1,3-dihydroxymethyl-2,5-dioxo-4-imidazolidinyl)-N'-(hydroxymethyl) urea (GERMALL™ II, diazolidinyl urea), imidazolidinyl urea (GERMALL™ 115), or 1,3-Bis(hydroxymethyl)-5,5-dimethylimidazolidine-2,4-dione (DMDM hydantoin, Glydant). These antimicrobials such as, for example, diazolidinyl urea are formaldehyde-releasing compounds that release a substantial amount of formaldehyde through decomposition.

The antimicrobial compound(s) may be employed in any ratio effective to combat microbial growth throughout the shelf-life of the composition, with very low to no formaldehyde, and further without adversely affecting the blood sample or cellular parameter to be measured by the selected analytical procedure. The amount of antimicrobial(s) may be employed in an effective amount to prevent microbial growth at ambient temperature through the shelf life of the concentrated reagent compositions and working concentration reagent compositions.

The combined antimicrobial agent(s) may be present in working concentration reagent at from 0.01 to 3 g/L, 0.1 to 2 g/L, or 0.5 to 1.8 g/L. The combined antimicrobial agent(s) may be present in concentrated reagent at from 0.1 to 50 g/L, 1 to 40 g/L, or 5 to 30 g/L. However, the amounts of individual antimicrobial agents may vary with potency.

5-Bromo-5-nitro-1,3-dioxane (Bronidox®) may be employed alone, or in combination with other antimicrobial agents, at from 0 to 1 g/L, 0.1 to 0.8 g/L, or 0.4 to 0.6 g/L in the working reagent composition or from 0 to 20 g/L, 1.0 to 16 g/L, or 4 to 12 g/L in aqueous concentrated reagent. Bronidox releases formaldehyde in a very small amounts and very slowly. Paulus, Microbicides for the protection of materials: a handbook, 1993, Pringer-Science+Business Media, B. V., Part III, Ch. 3, Formaldehyde releasing compounds, pp. 77-78.

A combination of 5-chloro-2-methyl-4-isothiazolin-3-one (CMIT) and 2-methyl isothiazolin-3-one (MIT) (as PROCLIN™ 150) may be employed at from 0 to 1 g/L, 0.1 to 0.8 g/L, or 0.4 to 0.6 g/L in a working concentration reagent composition, or from 0 to 20 g/L, 1.0 to 16 g/L, or 4 to 12 g/L in an aqueous concentrated reagent.

Certain antimicrobial agents are effective at lower concentrations than those described above. For example, in some aspects, polyaminopropyl biguanide (Cosmocil CQ®) and/or ortho-phthaldialdehyde (OPA), may each be employed in working concentration reagent at from 0 to 0.05 g/L, 0.01 to 0.03 g/L, or 0.015 to 0.025 g/L in a working reagent composition, or from 0 to 1 g/L, 0.10 to 0.60 g/L, or 0.15 to 0.5 g/L in an aqueous concentrated reagent.

Other antimicrobial agents may be similarly useful in compositions of this disclosure. Selection of such useful antimicrobial components is encompassed by this disclosure. Methods for determining the suitability of a particular antimicrobial agent in the composition of the present invention are found in U.S. Pat. No. 6,706,526 B2, incorporated by reference herein in its entirety.

Platelet Stabilizing Agent

The aqueous green concentrated reagents and green working concentration reagent compositions may optionally include a platelet stabilizing agent. The platelet stabilizing agent may be used to stabilize cell size, shape and integrity of blood cellular components, such as by preventing platelet aggregation. The precise quantities of the platelet stabilizing agent used may vary as dictated by their chemical formulation. Suitable platelet stabilizing agents include 4-aminobenzoic acid esters and derivatives thereof having the structures RHN—$C_6H_4$—COOR' or RHN—$C_6H_4$—COOCH$_2$CH$_2$R' where R is hydrogen and lower $C_{1-6}$ alkyl, and R' is lower alkyl, dialkylaminoalkyl and dialkylamino, where lower alkyl is $C_1$-$C_4$ alkyl and alkyl is $C_1$-$C_6$ alkyl. Examples of such compounds include benzocaine, procaine, butacaine, tetracaine and butethamine. These compounds are useful as a base or as a salt thereof, for example the hydrochloride, butyrate, nitrate or borate. In specific aspects, platelet stabilizer may be selected from 2-(dimethylamino) ethyl p-(butylamino)benzoate hydrochloride (Tetracaine hydrochloride) or 2-diethylaminoethyl 4-aminobenzoate hydrochloride (Procaine hydrochloride). The platelet stabilizing agent may be present in the working concentration reagent composition at from 0 to about 0.05 g/L, about 0.005 to about 0.05 g/L, or from about 0.01 to about 0.03 g/L. The platelet stabilizing agent may be present in the concentrated reagent composition at from 0 to about 2 g/L, about 0.05 to about 0.5 g/L, or from about 0.01 to about 0.03 g/L.

Osmotic Stabilizing Agents

An osmotic stabilizing agent may be optionally be employed in aqueous green concentrated reagent compositions and green working concentration reagents of the disclosure. Acceptable osmotic stabilizing agents include certain sugars, for example monosaccharides such as glucose, fructose, sorbose, xylose, ribose, and disaccharides such as sucrose, sugar-alcohols, such as mannitol, inositol, xylitol, and adonitol, glycerol, and certain amino acids such as glycine and arginine. The osmotic stabilizing agent may be, for example, glycerol. The osmotic stabilizing agent may optionally be employed at 0 to about 2 g/L, about 0.2 to about 1.5 g/L, or about 0.5 to about 1.5 g/L, in the working concentration reagent, or 0 to about 50 g/L, about 2 to about 30 g/L, or about 5 to about 25 g/L. The glycerol may be employed in working concentration reagents at 0 to about 1.6 mL/L, or about 0.5 to about 1.0 mL/L; or 0 to about 32 mL/L, or about 5 to about 20 mL/L in the concentrated reagent.

pH Adjusting Agents

The desired pH of the green working concentration reagent depends upon the hematology instrument utilized and the test to be performed. Preferably, the reagent will be adjusted during manufacture such that the pH of the reagent is from about 6 to about 8, about 6.5 to about 7.5, or about 6.9 to about 7.3. A pH adjusting agent may be employed in the concentrated reagent and/or working concentration reagent at a concentration sufficient to achieve the desired pH. The pH adjuster may be an alkaline metal hydroxide, for example sodium hydroxide or potassium hydroxide. In one aspect, the pH adjuster is 50% aq. NaOH. The pH adjuster may include an inorganic acid such as hydrochloric acid. In one aspect, the pH adjuster is 6N HCl. This concentration may be dependent on the concentration of other solutes that may contribute to the overall acidity or basicity of the reagent solution. One of skill in the art may readily determine the amount of base or acid required.

In some aspects, an aqueous green concentrated reagent is provided that upon dilution of from 10-fold to 20-fold, provides a green working concentration Reagent according to Table 1.

TABLE 1

| Inventive Working Concentration Reagent | | |
| --- | --- | --- |
| Component | range | Unit |
| Purified Water | 1 | L |
| TetraSodium EDTA | 2-3.5 | g |
| Sodium Sulfate | 2.5-5.5 | g |
| Potassium Sulfate | 1-2.5 | g |
| Sodium Phosphate Monobasic | 2.5-4.5 | g |
| Imidazole | 1-3 | g |
| Sodium Chloride | 1-3 | g |
| ProClin 150 | 0.3-0.6 | g |

TABLE 1-continued

| Inventive Working Concentration Reagent | | |
| --- | --- | --- |
| Component | range | Unit |
| L-Bronidox | 0.3-0.6 | g |
| 5-Fluoruracil | 0.3-1 | g |
| Sodium Potassium Tartrate | 6-8 | g |

Lytic Reagents

An ability to measure hemoglobin (Hgb) in blood samples is a routine part of diagnostic analysis and is also important for monitoring responsiveness to therapies directed towards diseases which affect hemoglobin and to therapies which are directed towards other diseases but which may have adverse side effects on the hemoglobin level. Leukocytes in the peripheral blood of normal subjects consist of five types, i.e., lymphocytes, monocytes, neutrophils, eosinophils and basophils. The latter three types of leukocytes are collectively referred to as granulocytes. Different types of leukocytes have different biological functionalities. Counting and differentiating different types of leukocytes in a blood sample provides valuable information for clinical diagnosis. For instance, an increased number of monocyte occurs either during the convalescence period of patients suffering from infectious diseases or in such diseases as monocytic leukemia.

The classification and counting of leukocytes has most commonly been conducted by the differential counting method which is also referred to the manual method. Automatic blood analyzers are also commonly used for counting leukocytes. Some automatic blood analyzers employ a hemolytic reagent to lyse erythrocytes and prepare a sample containing predominantly or solely leukocytes. The sample mixture then is analyzed, for example, by an impedance method. Some instruments count different types of leukocytes (differential counting) including monocytes, lymphocytes and granulocytes. Ideally, one would like to be able to accomplish multiple diagnostic analyses such as hemoglobin measurement and counting the numbers of leukocytes or differential counting of leukocyte subpopulations in a single automated step.

Among many well-known methods for hemoglobin determination, the cyanide hemoglobin method has been recommended as a standard by the International Committee for Standardization in Hematology. ICSH. Recommendations for haemoglobinometry in human blood. Br J Haematol. 1967; 13 (suppl:71-6). Modification of this method by Matsubara and Okuzono has led to its wide usage in clinical laboratories. Matsubara T, Okuzono H, Tamazawa S. Proposal for an improved reagent in the hemiglobincyanide method. In: Izak G, and Lewis, SM eds., Modern concepts in hematology. New York: Academic Press, 1972:29-42. In this method, the iron atoms of heme group in all forms of hemoglobin of the red cells are oxidized to methemoglobin by potassium ferricyanide. The methemoglobin is then complexed with cyanide anion, which has a very high affinity to iron ion of the heme group, to form a cyanmethemoglobin chromogen. This extremely stable chromogen has a maximum absorption at 540 nm, which is measured manually by UV spectrometry. However, because of the potassium cyanide used, the reagent waste has caused enormous environmental concern. Alternative automated hemoglobin analysis methods have been developed without utilizing cyanide.

The aqueous green working concentration reagents disclosed herein are appropriate for use with cyanide-free aqueous lytic reagents, as known in the art. A cyanide-free lytic reagent as known in the art may be employed along with working concentration reagents when used as a blood diluent in a hematology analyzer. Lytic reagents are described in U.S. Pat. Nos. 5,242,832, 5,763,280, 5,834,315, and 5,882,934, each of which is incorporated by reference herein.

U.S. Pat. No. 5,834,315 discloses a cyanide-free lytic reagent comprising a quaternary ammonium salt and/or a pyridinium salt in an amount effective to lyse erythrocytes for determining total hemoglobin in blood.

U.S. Pat. No. 5,242,832 discloses a cyanide-free lytic reagent for counting the number of leukocytes and measuring the hemoglobin concentration in blood samples. The lytic reagent is free of cyanides and includes a cationic surfactant such as a quaternary ammonium salt, an amphoteric surfactant or pyridinium salt, a buffer, and a hemoglobin stabilizer.

U.S. Pat. Nos. 5,763,280 and 5,882,934 disclose a cyanide-free lytic reagent composition comprising a hemolytic surfactant chosen from a quaternary ammonium salt or pyridinium salt and an organic ligand. The lytic reagent is mixed with a blood sample which is prediluted with a suitable sample diluent. Various hemoglobin ligands are also described.

EXAMPLES

Example 1. Formulations

Improved inventive aqueous green concentrated reagent compositions and green working concentration reagent compositions were prepared according to Tables 2 to 8 with the goal of being manufactured at a 10× to 20×concentration factor. In addition, reagent compositions were designed to exhibit low formaldehyde levels of no more than 2 ppm formaldehyde at manufacture and no more than 2 ppm formaldehyde after one year. Exemplary concentrated formulations are provided in this example.

TABLE 2

Inventive Aqueous Green Concentrated Reagent Composition A (15X) and 1X Green Working Concentration Reagent Composition

| Component | Range 1X | Range 15X | Unit |
| --- | --- | --- | --- |
| Purified Water | 1 | 1 | L |
| TetraSodium EDTA | 2-3.5 | 30-53 | g |
| Sodium Sulfate | 3.5-5.5 | 52.5-82.5 | g |
| Potassium Sulfate | 1.5-2.5 | 22.5-37.5 | g |
| Sodium Phosphate Monobasic | 3-4.5 | 45-67.5 | g |
| Potassium Bisulfate | 1-2 | 15-30 | g |
| Imidazole | 2.7-3 | 40.5-45 | g |
| Sodium Chloride | 2-2.5 | 30-37.5 | g |
| ProClin 150 | 0.3-0.6 | 4.5-9 | g |
| L-Bronidox | 0.3-0.6 | 4.5-9 | g |
| 5-Fluoruracil | 0.3-1 | 4.5-15 | g |
| Sodium Potassium Tartrate | 6-7 | 90-105 | g |

TABLE 3

Inventive Aqueous Green Concentrated Reagent Composition B (10X) and 1X Green Working Concentration Reagent Composition

| Component | Quantity/L 1X | Quantity/L 10X | Unit |
| --- | --- | --- | --- |
| Purified Water | 1 | 1 | L |
| TetraSodium EDTA | 2-3.5 | 20-35 | g |
| Sodium Sulfate | 5-6 | 50-60 | g |
| Potassium Sulfate | 5-5.5 | 50-55 | g |
| Imidazole | 2.5-3.0 | 25-30 | g |
| Sodium Chloride | 1-2 | 10-20 | g |
| ProClin 150 | 0.2-0.8 | 2-8 | g |
| Sodium Phosphate MonoBasic | 3-4 | 30-40 | g |
| HCl 6N | 2-2.5 | 20-25 | mL |
| Tetracaine HCl | 0.015-0.022 | 0.15-0.22 | g |
| Glycerol | 0.6-1.5 | 6-15 | mL |
| OPA | 0.02-0.03 | 0.2-0.3 | g |

TABLE 4

Inventive Aqueous Green Concentrated Reagent Composition C (15X) and 1X Green Working Concentration Reagent Composition

| Component | Quantity/L 1X | Quantity/L 15X | Unit |
| --- | --- | --- | --- |
| Purified Water | 1 | 1 | L |
| TetraSodium EDTA | 2-3.5 | 30-52.5 | g |
| Sodium Sulfate | 1.5-2.5 | 22.5-37.5 | g |
| Potassium Sulfate | 2.7-3.3 | 40-50 | g |
| Imidazole | 2.7-3.0 | 40-45 | g |
| Sodium Chloride | 1.4-1.8 | 20-27 | g |
| ProCiin 150 | 0.3-0.6 | 4.5-9 | g |
| Sodium Phosphate MonoBasic | 3-4 | 45-60 | g |
| HCl 6N | 2-2.5 | 30-37.5 | mL |
| Tetracaine HCl | 0.015-0.022 | 0.2-0.33 | g |
| Glycerol | 0.6-1.2 | 9-18 | mL |
| Sodium Potassium Tartrate | 13-15 | 195-225 | g |
| OPA | 0.01-0.02 | 0.15-0.3 | g |

TABLE 5

Inventive Aqueous Green Concentrated Reagent Composition D (15X) and 1X Green Working Concentration Reagent Composition

| Component | Quantity/L 1X | Quantity/L 15X | Unit |
| --- | --- | --- | --- |
| Purified Water | 1 | 1 | L |
| TetraSodium EDTA | 0.67-1.0 | 10-15 | g |
| Sodium Sulfate | 4-4.5 | 60-67.5 | g |
| Potassium Sulfate | 1.5-2.0 | 22.5-30 | g |
| Imidazole | 2.2-2.8 | 33-42 | g |
| Sodium Chloride | 2-2.3 | 30-34.5 | g |
| ProClin 150 | 0.3-0.7 | 4.5-10.5 | g |
| Sodium Phosphate MonoBasic | 2.8-3.1 | 42-46.5 | g |
| HCl 6N | 0.8-1.12 | 12-16.8 | mL |
| Tetracaine HCl | 0.015-0.022 | 0.22-0.33 | g |
| Glycerol | 0.5-1.0 | 7.5-15 | mL |
| Sodium Potassium Tartrate | 9-12 | 135-180 | g |
| Glutaraldehyde | 0.04-0.06 | 0.6-0.9 | g |

TABLE 6

Inventive Aqueous Green Concentrated Reagent Composition E (20X) and 1X Green Working Concentration Reagent Composition

| Component | Quantity/L 1X | Quantity/L 20X | Unit |
| --- | --- | --- | --- |
| Purified Water | 1 | 1 | L |
| TetraSodium EDTA | 0.8-1.2 | 16-24 | g |
| Sodium Chloride | 2.5-3.0 | 50-60 | g |
| Potassium Sulfate | 3.4-3.6 | 68-72 | g |

TABLE 6-continued

Inventive Aqueous Green Concentrated Reagent Composition E (20X) and 1X Green Working Concentration Reagent Composition

| Component | Quantity/L 1X | Quantity/L 20X | Unit |
|---|---|---|---|
| Imidazole | 2.6-3.0 | 52-60 | g |
| 6N HCl | 12-16 | 240-320 | g |
| Sodium Potassium Tartrate | 0.015-0.02 | 0.3-0.4 | g |
| OPA | 0.01-0.03 | 0.2-0.6 | g |

TABLE 7

Inventive Aqueous Green Concentrated Reagent Composition F (18X) and 1X Green Working Concentration Reagent Composition

| Component | Quantity/L 1X | Quantity/L 18X | Unit |
|---|---|---|---|
| Purified Water | 1 | 1 | L |
| TetraSodium EDTA | 2-3.5 | 36-63 | g |
| Sodium Sulfate | 2.5-5.5 | 45-99 | g |
| Potassium Sulfate | 1-2.5 | 18-45 | g |
| Sodium Phosphate MonoBasic | 2.5-3.5 | 45-63 | g |
| Imidazole | 1-2 | 18-36 | g |
| ProClin 150 | 0.4-0.6 | 7.2-10.8 | g |
| Bronidox | 0.4-0.6 | 7.2-10.8 | g |
| Sodium Chloride | 1-3 | 18-54 | g |
| 5-Fluorouracil | 0.3-1 | 5.4-18 | g |
| Sodium Potassium Tartrate | 7-8 | 126-144 | g |

TABLE 8

Inventive Aqueous Green Concentrated Reagent G (18X) and 1X Green Working Concentration Reagent Composition

| Component | Quantity/L 1X | Quantity/L 18X | Unit |
|---|---|---|---|
| Purified Water | 1 | 1 | L |
| TetraSodium EDTA | 2-3.5 | 36-63 | g |
| Sodium Sulfate | 2.5-5.5 | 45-99 | g |
| Potassium Sulfate | 1-2.5 | 18-45 | g |
| Sodium Phosphate MonoBasic | 2.5-3.5 | 45-63 | g |
| Imidazole | 1-2 | 18-36 | g |
| ProClin 150 | 0.4-0.6 | 7.2-10.8 | g |
| Sodium Chloride | 1-3 | 18-54 | g |
| Bronidox | 0.4-0.6 | 7.2-10.8 | g |
| Sodium Potassium Tartrate | 7-8 | 126-144 | g |

TABLE 9

Comparative Diluent

| Component | Quantity/L 1X | Unit |
|---|---|---|
| Purified Water | 1 | L |
| Imidazole | 2.5-3.0 | g |
| Sodium Sulfate | 13-15 | g |
| Sodium Chloride | 0.5-1.5 | g |
| ProClin 150 | 0.4-0.6 | g |
| EDTA Di Sodium | 2.5-3.5 | g |
| GERMALL ™ II | 0.7-0.8 | g |
| Tetracaine HCl | 0.01-0.02 | g |
| 6N HCl | 2.5-3.0 | g |

Each of the aqueous green concentrated reagent compositions A-G of Tables 2 to 8 were manufactured and stored in from 10× to 18×concentration factor as indicated and were stable for at least 12 months, or at least 18 months, when stored at a temperature selected from 2-30° C. The exemplary reagent compositions also exhibited low formaldehyde content at manufacture and after one year. For example, the concentrated reagent composition of Table 2 could be manufactured and stored at a 15×concentration factor and exhibited low formaldehyde levels of 0.1 ppm formaldehyde at manufacture and 0.2 ppm formaldehyde after one year.

In comparison, prior art comparative diluent according to Table 9 could only be manufactured at a maximum of 6×concentration factor because of limited component solubility and exhibited significantly higher formaldehyde levels in effluent after one year compared to inventive reagents.

Example 2. Lytic Reagents

Lytic reagents were prepared for use with each candidate working concentration reagent. Blood samples were diluted with working concentration reagents. The lytic reagent was prepared and mixed with a diluted blood sample to lyse red blood cells prior to analyzing white blood cells, for example, by using an automated differential analysis of white blood cells to determine at least three subpopulations of white blood cells. The lytic reagents were cyanide-free lytic reagent compositions comprising a hemolytic surfactant chosen from one or more quaternary ammonium salts and an organic ligand, for example, according to one or more of U.S. Pat. Nos. 5,763,280, 5,882,934, 5,834,315, and 5,935,857, each of which is incorporated by reference herein. The lytic reagents were tailored to each candidate working concentration reagent composition, as needed. For example, the amounts of one or more quaternary ammonium salts were optimized if needed.

Example 3. Characterization Tests and Materials

The limits of the aqueous green concentrated reagent physical parameters pH, conductivity osmolality and particle count were established in both ready to use (working concentration) and concentrated forms. Assessment of the manufacturability of the formulations and characterizing the raw materials was also performed. Additionally, a cycle time study and lytic reagent characterization was performed. Six DxH hematology analyzer systems with software versions 3.0.2 or higher were used to collect data and were employed at ambient temperature (19-27° C.). Normal whole blood specimens were collected in a potassium salt of EDTA.

Prior art commercially available reagents, calibrators and controls were employed for compatibility or comparison and included COULTER® DxH™ Diluent, COULTER® DxH™ Cleaner, COULTER® DxH™ CBC Lyse, COULTER® DxH™ Diff Pack, COULTER® DxH™ Retic Pack, COULTER® 6C control, COULTER® Retic Control, COULTER® Body Fluid, COULTER® Latron, and COULTER® SCal. Inventive 1×working concentration reagents and concentrated reagents were also investigated.

Functional testing was performed to establish the physical limits of the new reagent formulation, the pre-established legacy comparative diluent accuracy specifications were used. A formulation according to Table 2 was prepared in different working concentrations. Accuracy was determined by comparing the test working concentration reagent with the legacy comparative diluent at 1×run immediately before. A minimum of ten (10) normal blood specimens were collected. The instrument establishes a reference blank reading and compares to each sample blank to reference result. If the blank differs from reference by more than an allowable amount, the results are flagged with a review R flag. Any specimens that carried R flags were repeated, and the repetition used for the analysis. The acceptance criteria limits are those pre-established for the legacy comparative diluent accuracy limits.

Specifically, the green working concentration reagent composition of Table 2 was prepared at slightly higher concentration than 1× and through a series of dilutions to slightly lower than 1×, or from about +/−5% compared to 1×. Four instruments were used simultaneously, three run first with 1×comparative diluent of Table 9 then switched to the assigned test working concentration reagent. The fourth instrument was used as a comparator running comparative diluent at the same time as the test instruments were running test reagent. At the time the test instruments ran test reagents, the comparator ran legacy comparative diluent. This experiment was performed to identify possible issues with the blood aging process that may cause any measurement differences. This experiment was performed to account for any measurement differences that might arise due to the age of the samples, as characteristics of a blood sample can change over time.

The variation of the conductivity of acceptable dilutions of working concentration reagent was from 18.87 to 20.2 mS/cm; and osmolality was from 335 to 363 mOsm/Kg and these parameters were found to be linear with respect to concentration (data not shown). pH was from 7.15 to 7.16. Once this linearity was determined, Hematology Instrument System functional testing was performed. The measurements were performed at three different times due to the number of concentrations to be tested and the instrument availability. The accuracy and sample stability was assessed (data not shown). MCV, RDW and RDW-SD parameters were evaluated with respect to aged blood, test working concentration reagent at various dilutions of working concentration were compared to legacy 1×comparative diluent using fresh blood or aged blood samples for these parameters (data not shown).

The selected parameter (MCV, RDW and RDW-SD) results for test dilutions of working concentration reagent were found to be equivalent to comparative diluent for fresh normal and 24H blood. For green working concentration test reagents with concentrations slightly above 1× the results for test green working concentration reagent were better than comparative diluent.

Example 4. pH Ranges for Test Reagent

Characterization of pH range of concentrated reagent composition and working concentration reagent compositions according to Table 2 was performed. The final pH range of working concentration reagent compositions was initially set at target pH 6.9-7.3.

Two lots of aqueous green concentrated reagent compositions according to Table 2 at high pH (Lot AM) and low pH (Lot AN) were manufactured at 15× concentration. 1× dilutions provided the pH range of the green working concentration reagent composition. Two pools were prepared with differing concentrations of sodium phosphate monobasic to achieve the target characterization pH range extremes of pH 6.9 to 7.3. Results are shown in Table 10.

TABLE 10 pH Adjustments

| Lot # | Sodium Phosphate Monobasic added | Final pH Concentrate | pH at working concentration 1:15 |
|---|---|---|---|
| Lot AM High pH Test Reagent Composition | 2.3 g/L | 7.69 | 7.29 |
| Lot AN Low pH Test Reagent Composition | 5.0 g/L | 7.25 | 6.91 |

Lot AM test reagent was adjusted with water to meet the conductivity and osmolality specifications prior to performance evaluation on COULTER® DxH 800 Hematology Instruments of both high and low pH formulations with blood and controls. Low pH Lot AN test reagent required no adjustment for conductivity and osmolality. The high and low pH concentrated reagent compositions Lots AM and AN were adjusted for pH using 6N HCl (basic adjustment) and 50% sodium hydroxide (acidic adjustment). Each pool was adjusted to the target pH (7.10). The concentrated adjustment was calculated, adjusted and retested for correction to the pH.

Instrumentation performance evaluation of the high and low pH test reagents was performed at pH range extremes of 6.9-7.3. Final pool results for pH, osmolality and conductivity performance evaluation is shown in Table 11.

TABLE 11

Final adjustments

| Lot # | pH | Osmolality mOsm/Kg | Conductivity mS/cm |
|---|---|---|---|
| Lot AM | 7.29 | 334, 335 | 19.21 |
| Lot AN | 6.89 | 340, 340 | 19.45 |

Performance evaluation consisted of testing each working concentration reagent configuration with S-Cal Calibrator, Controls and 10 samples of fresh and 24 hour room temperature whole blood on DxH 800 Hematology Analyzers as follows. Test reagent compositions according to Table 2 were adjusted to high and low pH extremes of pH 6.9-7.30 range and performance was compared to comparative diluent of Table 9.

Performance testing of Lot AN low pH test reagent composition at pH 6.89 using normal fresh whole blood was performed and results were compared to performance of legacy Comparative diluent according to Table 9. The low pH 6.89 test formulation passed performance evaluation with respect to mean WBC, RBC, HGB, RDW, RDW-SD, PLT, MPV, NE, LY, MO, EO, BA, RET, MRV, and IRF test values that were comparable to comparative diluent of Table 9.

Performance testing of Lot AN low pH test reagent composition at pH 6.89 using aged normal 24 hour normal whole blood was performed and results were compared to performance of legacy comparative diluent according to Table 9. The low pH 6.89 test formulation passed performance evaluation exhibiting mean WBC, RBC, HGB, MCV, RDW, RDW-SD, PLT, MPV, NE, LY, MO, EO, BA, RET, MRV, and IRF test values that were comparable to comparative diluent of Table 9.

Performance testing of Lot AM high pH test reagent composition pH 7.29 using normal fresh whole blood was performed and results were compared to performance of legacy comparative diluent according to Table 9. The high pH 7.29 test formulation passed performance evaluation exhibiting mean WBC, RBC, HGB, MCV, RDW, RDW-SD, PLT, MPV, NE, LY, MO, EO, BA, RET, MRV, and IRF test values that were comparable to comparative diluent according to Table 9.

Performance testing of Lot AM high pH test reagent pH 7.29 using aged normal 24 hour normal whole blood was performed and results were compared to performance of Comparative diluent according to Table 9. The high pH 7.29 test formulation passed performance evaluation exhibiting mean WBC, RBC, HGB, MCV, RDW, RDW-SD, PLT, MPV, NE, LY, MO, EO, BA, RET, MRV, and IRF test values that were comparable to comparative diluent formulation of Table 9. However, the high pH test reagent failed when compared to legacy comparative diluent for MCV, RDW-SD difference values for aged blood, and at low pH there was failure on MCV. However, test reagent pH values from pH 7.02 to 7.20 were found to be acceptable in each parameter.

Next the conductivity adjusters were established for the pooling process. It was necessary to demonstrate that the performance of the adjusted reagent complies with the pre-establish accuracy limits for test reagent. When the conductivity is high the adjustment consists of diluting the pool with deionized water. This case was shown in a low and high concentration study that was performed.

Adjusters NaCl and $Na_2SO_4$ were added to a slightly diluted working concentration reagent (96% of 1×) according to Table 2, having low conductivity as shown in Table 12. This study was used to establish not only the adjusters but also the adjustable limits of the pooling process. The results are discussed below.

The low concentration NaCl and low concentration $Na_2SO_4$ Adjusted Pool were compared to comparative diluent of Table 9. All adjusted reagent compositions passed all accuracy specifications, including MCV of aged samples which is one of the most difficult to control (data not shown). The NaCl adjusted pool showed slightly better instrument performance than the sulfate adjusted pool.

Table 12 shows the physical parameters and the amount of adjuster used for each case. The sodium chloride adjusted pool kept the conductivity/osmolality ratio closer to the target formulation and, in addition, less amount of the adjuster was needed.

TABLE 12

Conductivity Adjuster amounts

|  | 96% | Adjusted NaCl | Adjusted $Na_2SO_4$ |
|---|---|---|---|
| pH | 7.14 | 7.15 | 7.16 |
| Cond | 18.93 | 19.64 | 19.84 |
| Osm | 337 | 350 | 352 |
| Amount of adjuster | 0.00 | 0.49 g/L | 1.03 g/L | pH Range adjustment of test aqueous green reagents according to Table 2 in concentrated and working solution forms can be adjusted for basic and acidic conditions with 6N HCl (basic adjustment) and 50% Sodium Hydroxide (acidic adjustment).

All Controls tested recovered within acceptable ranges. The MCV value for the S-Cal calibrator and 6C controls were lower at pH 6.9 with 5 g/L Sodium Phosphate Monobasic. All other parameters for fresh and 24 hour blood met the pre-established specifications for the commercial DxH comparative diluent.

The characterization of the pH range showed an adjustable range of pH 6.9 to 7.30, and a specification range of pH 7.00 to 7.20.

Example 5. Osmolality and Conductivity Adjusters for Test Reagent

Assays were performed to characterize the response of the test reagents according to Table 2 to adjustments targeting changes to the pH, osmolality and conductivity of the reagent test pools.

Each of the test pools were adjusted for osmolality and conductivity with different chemicals, for example, sodium chloride, sodium sulfate, potassium sulfate, potassium bisulfate, imidazole and sodium phosphate monobasic. Adjusting for osmolality or conductivity parameters impacts all three parameters of pH, conductivity and osmolality.

Variation of pH, conductivity and osmolality was observed by adding increasing amounts of each adjuster to a test reagent pool. Amounts of each adjuster to achieve target midpoint were established. The target pH, osmolality and conductivity were pH 7.02-7.20, target osmolality 315-360 mOsm/Kg, and target conductivity 19.05-20.00 mS/cm.

The impact of each adjuster on working concentration reagent as shown in Tables 13 and 14.

TABLE 13

Example Osmolality and Conductivity Adjusters

| Adjuster | ▲ pH/gm | ▲ Osmolality mOsm/kg/gm | ▲ Conductivity mS/cm/gm |
|---|---|---|---|
| Potassium Sulfate | +0.02 | +11.9 | +1.07 |
| Sodium Chloride | 0.00 | +29.2 | +1.61 |
| Sodium Sulfate | +0.01 | +14.1 | +0.88 |

TABLE 14

Example pH Adjusters

| Adjuster | ▲ pH/gm | A Osmolality mOsm/kg/gm | ▲ Conductivity mS/cm/gm |
|---|---|---|---|
| Imidazole | +0.21 | +24.9 | +0.28 |
| Sodium Phosphate Mono | −0.14 | +12.0 | +0.46 |
| 50% Sodium Hydroxide | +0.39 | +13.7 | +0.38 |
| 6N Hydrochloric Acid | −0.16 | +7.0 | +0.33 |

Conductivity Response to Temperature

The effect of variation of the conductivity response with the changes of temperature followed a linear function in the test reagent. Therefore, the linear function's slope was determined, so the temperature compensation factor could be adjusted. Three solutions of different conductivities (therefore different concentrations) within the accepted limits of the diluting unit were prepared to assess the response of each of them.

The change variation of conductivity of the final formulation with the temperature was characterized using three different concentrations. Solutions with 19.60 mS/cm, 19.70 mS/cm and 19.80 mS/cm at 25° C. were used. The conductivity response to temperature variation was measured for each solution at temperatures from 6.9 to 33.9° C., 10.7 to 37.7° C., and 10 to 38° C., respectively, using two different types of conductivity meters. The response of the conductivity with the variation of the temperature was linear for all three solutions. The linear regression equations were very similar and the R square values were better than 0.99 for all three cases.

All pH, conductivity and osmolality adjusters functioned as expected with no precipitation. Target values for each physical parameter of pH, conductivity and osmolality were achieved with all adjusters used.

Sodium chloride or sodium sulfate were selected to adjust the osmolality and conductivity of test concentrated reagent or test working concentration reagents. Both adjusters (NaCl and $Na_2SO_4$) were shown to be acceptable, but the sodium chloride proved to be more effective at keeping a better conductivity/osmolality ratio and better controlling the MCV for 24H blood. Therefore sodium chloride is the preferred adjuster for low conductivity and low osmolality pools. The adjustable ranges established for 100±4% pool concentrations are 19.70 mS/cm±0.8 mS/cm for conductivity and 350±13 mOsm/Kg for the osmolality.

pH adjustment from acidic values of 6.9 to 7.1 employed 50% sodium hydroxide to achieve target value of 7.15. pH adjustment from basic value of 7.3-7.2 employed 6N HCl to achieve target value of 7.15

Example 6. Hemoglobin Stability

A test was performed to characterize the impact of the diluent change from comparative diluent according to Table 9 to test green working concentration reagent according to Table 2 with respect to the stability of the hemoglobin complex. A diluent that destabilizes the hemoglobin complexes in a blood sample could result in erroneously low hemoglobin measurements. The complex formed by the imidazole and hemoglobin is stable with the variation of temperature. A control sample was used to prove the validity of the method and two fresh whole normal blood samples were used to compare the stability of the complex at the extremes of the instrument temperature claims. Specifically, 6C control level 3 and two fresh normal samples were tested with Comparative diluents and Test Reagent with Cell Lyse at 23° C. and 32° C. Results are shown in Table 15.

TABLE 15

Hemoglobin Stability with Temperature variation on Spectrophotometer

| Sample | Temp | Absorbance Mean | Mean diff |
|---|---|---|---|
| 6CL3 | 23° C. | 0.447967 | −2.02% |
| | 32° C. | 0.438933 | |
| Donor 1 Comparative Diluent | 23° C. | 0.376467 | 1.81% |
| | 32° C. | 0.369667 | |
| Donor 1 Test Reagent | 23° C. | 0.376133 | −1.89% |
| | 32° C. | 0.369033 | |
| Donor 2 Comparative Diluent | 23° C. | 0.340667 | −1.27% |
| | 32° C. | 0.336333 | |
| Donor 2 Test Reagent | 23° C. | 0.3332 | −1.65% |
| | | 0.3277 | |

As shown in Table 15, differences between the temperature extremes were less than 2% and the differences between test reagents and comparative diluent were less than 0.4% between temperature conditions, demonstrating that the hemoglobin complex is stable with the variation of temperature. The hemoglobin stability was confirmed. The test reagent proved to be equivalent to the comparative diluent with a difference smaller than 0.4% which is within the accuracy acceptance criteria.

Example 7. Fish Toxicity Test

The purpose of the test was to determine acute toxicity effects towards fish. Samples of working concentration test sample reagent and concentrated reagent were sent to aquatic testing lab to assess the marine life toxicity. Both concentrated and working concentration test reagents passed the fish toxicity test. In both cases the $LC_{50}$ of the reagents is above 750 mg/L exceeding acceptance criteria. Waste is hazardous by acute aquatic toxicity if a 96-hour $LC_{50}$ is less than 500 mg/liter according to California State water hazardous regulations. Both reagents demonstrated low acute toxicity to fish and were able to pass the fish toxicity test required by the California State water hazardous regulations.

Example 8. Cyanide Test

The concentrated test reagent composition according to Table 2 was subjected to trace analysis. The total cyanide level was 0.005 ppm when tested according to EPA method 335.4. Therefore the concentrated reagent composition was considered to be cyanide-free.

What is claimed is:

1. A concentrated reagent composition comprising:
   a metal sulfate;
   a phosphate-based buffer;
   a hemoglobin ligand; and
   an antimicrobial agent;
   wherein the concentrated reagent composition is diluted with water by a dilution factor of between 10 and 20 to provide a working concentration reagent composition, wherein the working concentration reagent composition is used in a hematology analyzer for analyzing cells.

2. The concentrated reagent composition of claim 1, further comprising a chelating agent.

3. The concentrated reagent composition of claim 2, wherein the composition comprises 10 to 100 g/L of a chelating agent, wherein the chelating agent is tetrasodium EDTA; 10 to 50 g/L a hemoglobin ligand, wherein the hemoglobin ligand is imidazole; 20 to 100 g/L of a first alkaline metal sulfate, wherein the first alkaline metal sulfate is sodium sulfate; 15 to 60 g/L of a second alkaline metal sulfate, wherein the second alkaline metal sulfate is potassium sulfate; 10 to 80 g/L of a phosphate-based buffer, wherein the phosphate-based buffer is sodium phosphate monobasic; and an antimicrobial agent selected from the group consisting of 5-chloro-2-methyl-4-isothiazolin-3-one (CMIT), 2-methyl-4-isothiazolin-3-one (MIT), 5-bromo-5-nitro-1,3-dioxane, and 5-fluorouracil.

4. The concentrated reagent composition of claim 3, further comprising 60 to 300 g/L sodium potassium tartrate.

5. The concentrated reagent composition of claim 1, wherein the composition comprises or produces less than about 2 parts per million (ppm) of formaldehyde over a period of time of at least 1 year when stored at ambient temperature.

6. The concentrated reagent composition of claim 1, wherein the metal sulfate is selected from the group consisting of sodium sulfate, potassium sulfate, potassium hydrogen sulfate, and sodium hydrogen sulfate.

7. The concentrated reagent composition of claim 6, further comprising sodium sulfate and potassium sulfate and a weight ratio of sodium sulfate to potassium sulfate is from 0.5:1 to 3:1.

8. The concentrated reagent composition of claim 6, wherein the working concentration reagent composition comprises from 25 to 75 mmol total sulfate anion.

9. The concentrated reagent composition of claim 1, wherein the hemoglobin ligand is selected from the group consisting of imidazole, phenylimidazole, methylimidazole, ethylimidazole and butylimidazole.

10. The concentrated reagent composition of claim 1, wherein the phosphate-based buffer is selected from one or more of, potassium hydrogen phosphate, sodium hydrogen phosphate, sodium phosphate monobasic, or a hydrate thereof.

11. The concentrated reagent composition of claim 1, wherein the antimicrobial agent is selected from the group consisting of 5-fluorouracil, 5-chloro-2-methyl-4-isothiazolin-3-one (OMIT), 2-methyl-4-isothiazolin-3-one (MIT), 5-bromo-5-nitro-1,3-dioxane, polyaminopropyl biguanide, 1,2-benzisothiazolin-3-one (BIT), 4,5-dichloro-2-n-octyl-4-isothiazolin-3-one (DCOIT), 2-n-octyl-4-isothiazolin-3-one (OTT), ortho-phthaldialdehyde (OPA), and 1,2 dibromo-2,4 dicyanobutane.

12. The concentrated reagent composition of claim 1, wherein the composition further comprises one or more of the group consisting of an alkaline metal chloride, a platelet stabilizing agent, and an osmotic stabilizing agent.

13. The concentrated reagent composition of claim 1, wherein upon aqueous dilution selected from at least 10-fold to 20-fold to form the working concentration reagent composition, the working concentration reagent composition exhibits each of: i) pH 6.90 to 7.30 at ambient temperature; ii) conductivity of 19.05 to 20.00 mS/cm at ambient temperature; and iii) osmolality of 315 to 360 mOsm/Kg at ambient temperature.

14. A method for analyzing a biological sample comprising:
providing a concentrated reagent composition having a metal sulfate, a phosphate-based buffer, a hemoglobin ligand, and an antimicrobial agent;
diluting the concentrated reagent composition with water by a dilution factor from between 10-fold to 20-fold to form a working concentration reagent composition;
utilizing a hematology analyzer to mix a biological sample with the working concentration reagent composition to form a diluted biological sample; and,
analyzing the diluted biological sample to determine at least one physical parameter of the sample.

15. The method of claim 14, wherein the biological sample is a blood sample containing blood cells, the diluted biological sample is a diluted blood sample, the concentrated reagent composition further comprises a chelating agent, and the chelating agent and the hemoglobin ligand are in an amount effective to provide reproducible hemoglobin and cell volume measurements over a temperature range from 15° C. to 32° C.; and wherein the method further comprises analyzing the diluted blood sample to determine at least one physical parameter of the blood cells.

16. The method of claim 15, wherein the blood cells comprise red blood cells and/or white blood cells.

17. The method of claim 15, wherein the analyzing the diluted blood sample to determine at least one physical parameter comprises analyzing to determine mean cell volume of the blood cells.

18. The method of claim 15, further comprising mixing a lytic reagent with the diluted blood sample to lyse red blood cells prior to the analyzing of the diluted blood sample.

19. The method of claim 15, wherein the analyzing of the diluted blood sample to determine at least one physical parameter of the blood cells comprises an automated differential analysis of white blood cells to determine at least three subpopulations of white blood cells.

20. The method of claim 15, wherein the analyzing of the diluted blood sample to determine at least one physical parameter comprises analyzing to determine a number of platelets or analyzing to determine hemoglobin content.

* * * * *